US00PP22980P2

(12) United States Plant Patent
Keogh

(10) Patent No.: US PP22,980 P2
(45) Date of Patent: Aug. 21, 2012

(54) *TIBOUCHINA* PLANT NAMED 'TEKO'

(50) Latin Name: *Tibouchina×hybrida*
Varietal Denomination: TEKO

(76) Inventor: Terence Keogh, Victoria Point (AU)

( * ) Notice: Subject to any disclaimer, the term of this patent is extended or adjusted under 35 U.S.C. 154(b) by 0 days.

(21) Appl. No.: 13/135,590

(22) Filed: Jul. 11, 2011

Related U.S. Application Data

(60) Provisional application No. 61/400,190, filed on Jul. 26, 2010.

(51) Int. Cl.
*A01H 5/00* (2006.01)

(52) U.S. Cl. ..... Plt./263.1; Plt./226

(58) Field of Classification Search ..... Plt./263.1, Plt./226
See application file for complete search history.

*Primary Examiner* — June Hwu
*Assistant Examiner* — Louanne Krawczewicz Myers

(57) ABSTRACT

A new cultivar of *Tibouchina* named 'TEKO' that is characterized by rounded compact habit, ornamental green foliage that exhibits marked longitudinal ribbing and a profuse display of large vibrant violet flowers and red buds over a long bloom period. In combination these traits set 'TEKO' apart from all other existing varieties of *Tibouchina* known to the inventor.

2 Drawing Sheets

Genus: *Tibouchina.*
Species: ×*hybrida.*
Denomination: 'TEKO'.

BACKGROUND OF THE INVENTION

This application claims the benefit of priority under 35 U.S.C. 119(e) of U.S. Provisional Application No. 61/400,190 filed on Jul. 26, 2010 entitled *Tibouchina* plant named 'TEKO'.

The present invention relates to a new and distinct cultivar of *Tibouchina*, commonly known as Princess Flower or Glory Bush which is grown as an ornamental evergreen tropical flowering shrub for planting in the landscape or in containers. The new cultivar, in the family Melastomataceae, is known botanically as *Tibouchina×hybrida* and will be referred to hereinafter by the cultivar name 'TEKO'.

'TEKO' is derived from an ongoing breeding program which has been conducted by the inventor for more than thirty years at the inventor's nursery in Victoria Point, Queensland, Australia. The objective of the breeding programme is to produce novel varieties of *Tibouchina* in varying plant sizes, flower colors and which are well-suited to a range of climate zones. 'TEKO' is a hybrid plant derived from the deliberate controlled cross-pollination of the female parent, an individual seedling of *Tibouchina organensis* (species, unpatented) and the male parent, an individual plant of *Tibouchina mutabilis* 'Jazzie' (unpatented). The inventor emasculated flowers of the female parent and applied pollen which was freshly collected from the male parent. The parent plants were isolated to prevent open pollination. In 2004 the inventor selected 'TEKO' as a seedling which had been raised from the cross-pollination described above. Selection was based on the criteria of habit and plant dimensions. The closest two comparison plants known to the inventor are the two parents. Whereas the female parent can grow to a mature height of 3 meters, and the male parent can achieve a height of 2 meters, mature plants of 'TEKO' have not been observed to exceed a height of 1 meter.

*Tibouchina×hybrida* 'TEKO' exhibits distinctly rounded compact habit, strong basal branching, foliage with marked longitudinal ribbing, and a prolific simultaneous display of red buds and large single flowers that are vibrant violet in color. Typically 'TEKO' blooms over a long period summer through fall. Under the most favorable conditions blooming can occur sporadically throughout the year. Cultural conditions include freely draining moisture retentive soil, with regular sunlight and water. Hardiness is USDA Zone 10 and warmer. Once established 'TEKO' is heat and drought tolerant, and at maturity reaches 1 meter in height.

'TEKO' was first asexually reproduced by the inventor in Victoria Point, Queensland, Australia. Asexual propagation was accomplished in 2009 using tip cuttings. Since that time, under careful observation, the distinguishing characteristics of 'TEKO' have been determined stable and uniform, and reproduce true to type in successive generations of asexual propagation.

SUMMARY OF THE INVENTION

The following represent the distinguishing characteristics of 'TEKO'. In combination these traits set 'TEKO' apart from all other existing varieties of *Tibouchina* known to the inventor. 'TEKO' has not been tested under all possible conditions and phenotypic differences may be observed with variations in environmental, climatic, and cultural conditions, however, without any variance in genotype.

1. 'TEKO' grows with a distinctly rounded compact habit exhibiting strong basal branching.
2. After one year of growth 'TEKO' is approximately 46 cm in height and 38 cm in width.
3. At maturity, 'TEKO' is 1 meter in height and 1 meter in width.
4. The foliage of 'TEKO' exhibits marked longitudinal ribbing.
5. 'TEKO' bears buds and flowers simultaneously in profusion and continually over a long blooming period from summer through fall.

6. The flowers of 'TEKO' are large, single, and vibrant violet in color.
7. The flower buds of 'TEKO' are red in color.
8. 'TEKO' is heat and drought tolerant once established.
9. 'TEKO' survives in USDA Hardiness Zone 10 and warmer.

BRIEF DESCRIPTION OF THE DRAWINGS

The accompanying color drawings illustrate the overall appearance of 'TEKO' showing the color of foliage and flower as true as it is reasonably possible to obtain in color reproductions of this type.

Drawing labeled

Drawing labeled

Figure 1:
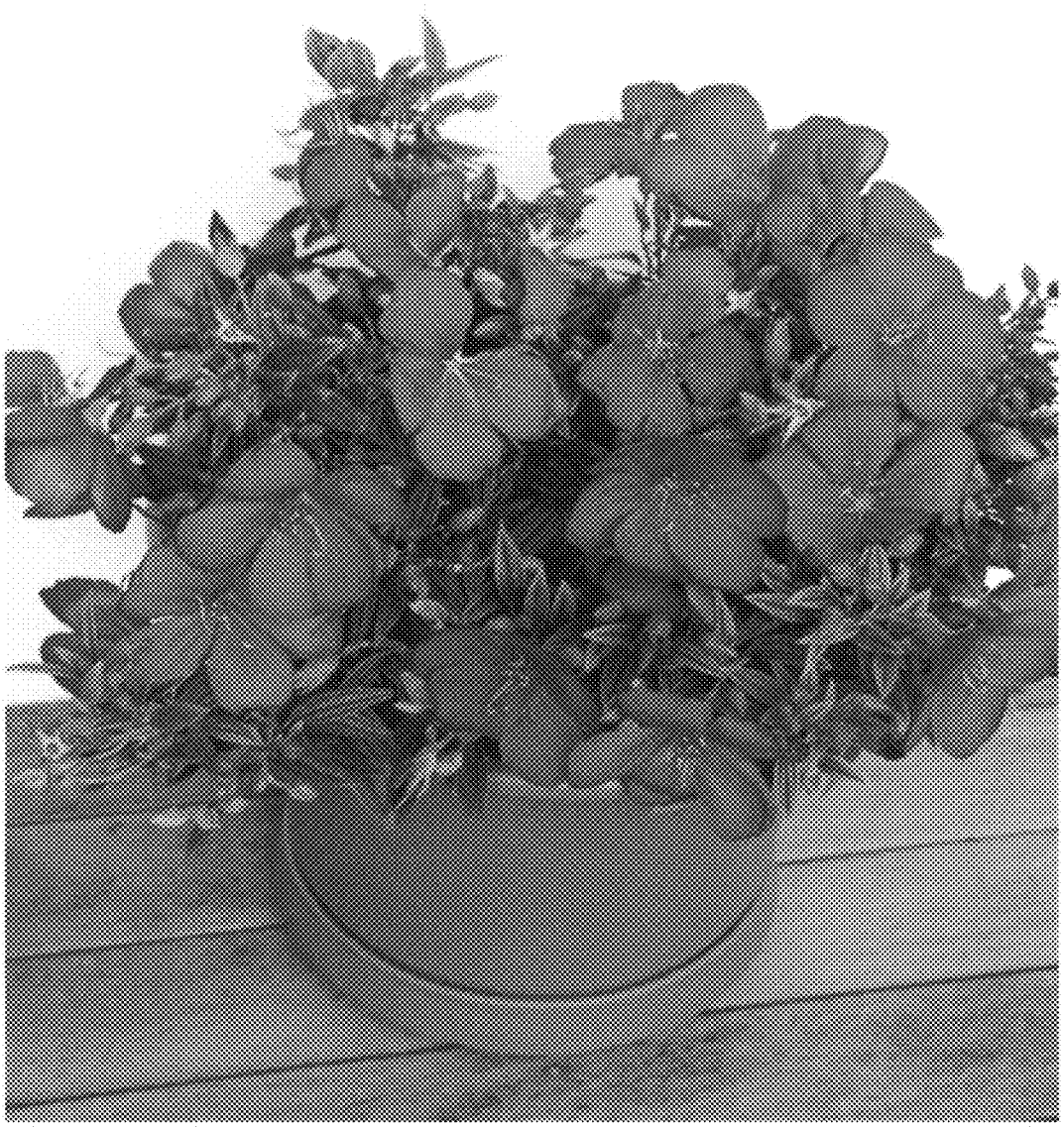
FIG. 1 depicts a one-year-old plant of 'TEKO' growing in a 1-litre container in a frost-free greenhouse in Melbourne, Australia.
Figure 2:
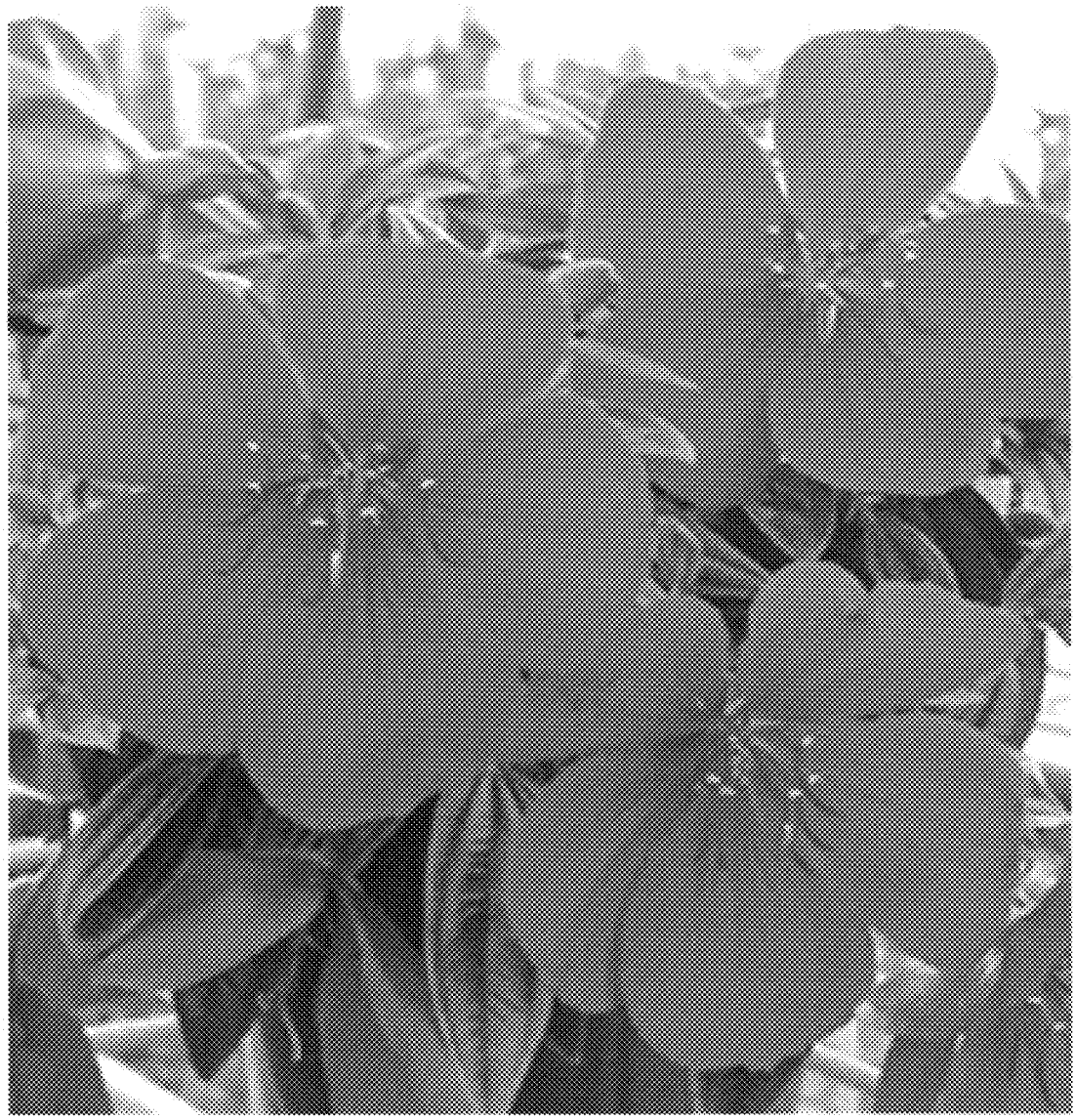
FIG. 2 depicts a close-up view of a flower of 'TEKO' flower.

Drawings were made using conventional techniques and although color may appear different from actual colors due to light reflectance, they are as accurate as possible by conventional photography.

BOTANICAL DESCRIPTION OF THE PLANT

The following is a detailed description of the new *Tibouchina* cultivar named 'TEKO'. Data was collected in Arroyo Grande, Calif. from a 9-month-old 1-litre greenhouse grown container plant. Color determinations are in accordance with the 2007 Edition of The Colour Chart of The Royal Horticultural Society, London, England, except where general color terms of ordinary dictionary significance are used. The growing requirements are similar to the species. There is no pest or disease susceptibility nor resistance known to the inventor.

Botanical classification: *Tibouchina*×*hybrida* 'TEKO'.
Genus: *Tibouchina.*
Species: ×*hybrida.*
Denomination: 'TEKO'.
Family: Melastomataceae.
Common name: Princess Flower or Glory Bush.
Use: For use in landscape and container.
Parentage: *Tibouchina*×*hybrida* 'TEKO' is a hybrid plant resulting from the controlled cross-pollination of the following parents.
- *Female parent*.—An individual *Tibouchina organensis* (species, unpatented).
- *Male parent*.—An individual *Tibouchina mutabilis* 'Jazzie' (unpatented).

Vigor: Vigorous.
Growth habit: Distinctly rounded compact habit.
Commercial category: Dwarf shrub.
Plant dimensions (at one year): 46 cm in height and 38 cm in width.
Plant dimensions (at maturity): 1 meter in height and 1 meter in width.
Hardiness: USDA Hardiness Zone 10 and warmer.
Propagation: Tip cuttings.
Root system: Fine and fibrous.
Cultural requirements: Plant in freely draining moisture retentive fertile soil, with regular water and sunlight.
Special considerations: Protect from hottest areas of direct sunlight. Drought tolerant once established.
Time to initiate roots (range): 14-28 days to produce roots on an initial cutting.
Crop time (average): 9 months to produce a 1-litre container plant from a rooted cutting.
Seasonal interest: Simultaneous display of red buds and large vibrant violet flowers that bloom over a long period, and ornamental leaves with marked longitudinal pattern.

Stem:
- *Branching habit*.—Strong basal branching.
- *Main stem dimensions.*—4 cm in height and 0.50 cm in diameter.
- *Lateral stem dimensions* (*average*).—11 cm in length and 3 mm in diameter.
- *Lateral branch quantity* (*average*).—11 in number.
- *Internode length* (*range*).—0.70 cm to 1 cm.
- *Shape*.—Cylindrical.
- *Surface*.—Scurfy.
- *Branch color.*—199D.

Foliage:
- *Leaf quantity* (*average*).—30 leaves per branch.
- *Leaf arrangement*.—Opposite.
- *Leaf division*.—Simple.
- *Leaf margin*.—Entire.
- *Leaf shape*.—Elliptic.
- *Leaf base*.—Attenuate.
- *Leaf apex*.—Acute.
- *Leaf venation pattern.*—3 primary parallel veins.
- *Vein color* (*adaxial surface*).—147A.
- *Vein color* (*abaxial surface*).—146D.
- *Leaf surface* (*adaxial*).—Puberulent with veins depressed.
- *Leaf surface* (*abaxial*).—Pubescent with veins protruding.
- *Leaf texture* (*adaxial surface*).—Prominently ribbed.
- *Leaf texture* (*abaxial surface*).—Prominently ribbed.
- *Leaf attachment*.—Petiolate.
- *Petiole length* (*range*).—0.75 cm to 1.50 cm in length.
- *Petiole diameter* (*average*).—<1 mm. in diameter.
- *Petiole color.*—199D.
- *Petiole surface*.—Pubescent.
- *Petiole shape*.—Cylindrical.
- *Leaf length* (*range*).—0.60-5 cm.
- *Leaf width* (*range*).—1.10-2 cm.
- *Leaf color* (*adaxial surface*).—Three bands of 147A (along and either side of each of the three longitudinal veins; 151A elsewhere and at the margin.
- *Leaf color* (*abaxial surface*).—146B.
- *Foliar fragrance*.—None observed to date.

Inflorescence:
- *Inflorescence type*.—Solitary.
- *Inflorescence shape*.—Rotate.
- *Inflorescence dimensions.*—7.50 cm in diameter and 3.50 cm in depth.
- *Quantity* (*average*).—20 per 1-litre container plant.
- *Aspect*.—Facing upward and outward.
- *Number of petals.*—5 in number.
- *Petal color* (*both surfaces*).—Ranges between N81A and N81D.
- *Petal length.*—4.40 cm.
- *Petal width.*—3.40 cm.
- *Petal margin*.—Entire.
- *Petal apex*.—Obtuse.
- *Petal base*.—Attenuate.
- *Petal shape*.—Obdeltoid.
- *Petal surface* (*abaxial and adaxial*).—Glabrous.
- *Petals fused or unfused*.—Unfused.
- *Bud shape*.—Elliptic.

*Bud color.*—180A.
*Bud surface*.—Pubescent.
*Bud apex*.—Acute.
*Bud quantity* (*range*).—50-70 buds per 1-litre container plant.
*Bud length.*—2.50 cm.
*Bud diameter.*—0.90 cm.
*Persistent or self-cleaning*.—Self-cleaning.
*Shape of calyx.*—Cupule.
*Calyx color*.—Ranges between 189B to N79D as bud develops and flower opens.
*Dimensions of calyx.*—0.70 cm in diameter and 0.80 cm in length.
*Sepal quantity.*—5 in number.
*Sepal dimensions.*—1.05 cm in length and 0.50 cm in width.
*Sepal surface* (*adaxial*).—Lanate.
*Sepal surface* (*abaxial*).—Puberulent.
*Color of hairs.*—197D.
*Sepal color* (*adaxial surface*).—180A.
*Sepal color* (*abaxial surface*).—180A.
*Sepal margin*.—Entire.
*Sepal apex.*—Acute.
*Sepal base*.—Truncate.
*Sepals fused or unfused*.—Unfused.
*Blooming period*.—Summer through fall. Can bloom sporadically through the year in the most favorable conditions.
*Peduncle dimensions.*—1 cm in length and 2 mm in diameter.
*Peduncle shape*.—Cylindrical.
*Peduncle color*.—Ranges between N81C and 189B.
*Peduncle surface*.—Lanate.
*Inflorescence fragrance*.—None observed to date.

Reproductive organs:
*Stamens.*—10 in number.
*Stamen color.*—84B.
*Stamen dimensions.*—2 cm in length and 1 mm in diameter.
*Anther color*.—Ranges between N89A and 155A.
*Anther shape*.—Sickle.
*Anther length.*—1 cm.
*Pollen quantity*.—None observed to date.
*Pistil.*—1 in number.
*Pistil shape*.—Columnar.
*Pistil color.*—180B.
*Pistil dimensions.*—2 cm in length and 1 mm in diameter.
*Stigma shape*.—Blunt.
*Stigma color.*—155A.
*Stigma length.*—0.10 cm.
*Ovary color.*—138B.
*Ovary dimensions.*—1 cm in height and 0.70 cm in width.
*Ovary shape*.—Cupule.
*Ovary surface*.—Lanate.
*Ovary position*.—Inferior.

Seed: Seed has not been found during repeated observations.

The invention claimed is:

1. A new and distinct variety of *Tibouchina* plant named 'TEKO' as described and illustrated herein.

* * * * *